United States Patent [19]

Manschot et al.

[11] 4,244,920

[45] Jan. 13, 1981

[54] SPECIMEN COLLECTION ASSEMBLY

[75] Inventors: James G. Manschot, Eagle; Lawrence A. Salvadori; Byron L. Mather, both of Milwaukee, all of Wis.

[73] Assignee: Plastronics, Inc., Milwaukee, Wis.

[21] Appl. No.: 101,699

[22] Filed: Dec. 10, 1979

Related U.S. Application Data

[63] Continuation-in-part of Ser. No. 910,643, May 30, 1978, abandoned.

[51] Int. Cl.[3] .................. B01L 3/00; B65D 41/04; B65D 41/18
[52] U.S. Cl. .................. 422/102; 128/272; 128/760; 220/288; 220/306; 220/354
[58] Field of Search .................. 422/99, 102; 220/288, 220/306, 352, 354, 355, 356; 128/272, 295, 760

[56] References Cited

U.S. PATENT DOCUMENTS

| | | | |
|---|---|---|---|
| 3,117,691 | 1/1964 | Williams | 220/306 |
| 3,633,789 | 1/1972 | Markowitz | 220/306 |
| 3,881,465 | 5/1975 | Raitto | 128/295 X |
| 4,130,220 | 12/1978 | McKirnan | 220/306 |

FOREIGN PATENT DOCUMENTS

| | | | |
|---|---|---|---|
| 996266 | 8/1951 | France | 220/288 |
| 2252751 | 6/1975 | France | 220/288 |

*Primary Examiner*—Joseph Scovronek
*Attorney, Agent, or Firm*—Michael, Best & Friedrich

[57] ABSTRACT

A specimen collection assembly comprising a cup member having a body portion and an open end closure portion. The assembly also includes a cap member having a closure portion adapted for engagement with the cup closure portion to effectuate a seal between the cap member and the cup member to thereby seal the interior of the cup body portion. The cup and cap members each have an outer protective wall thereon extending past and covering the outermost extremities of the closure portions of the cup and cap members to protect the closure portions from hand and body contact.

13 Claims, 11 Drawing Figures

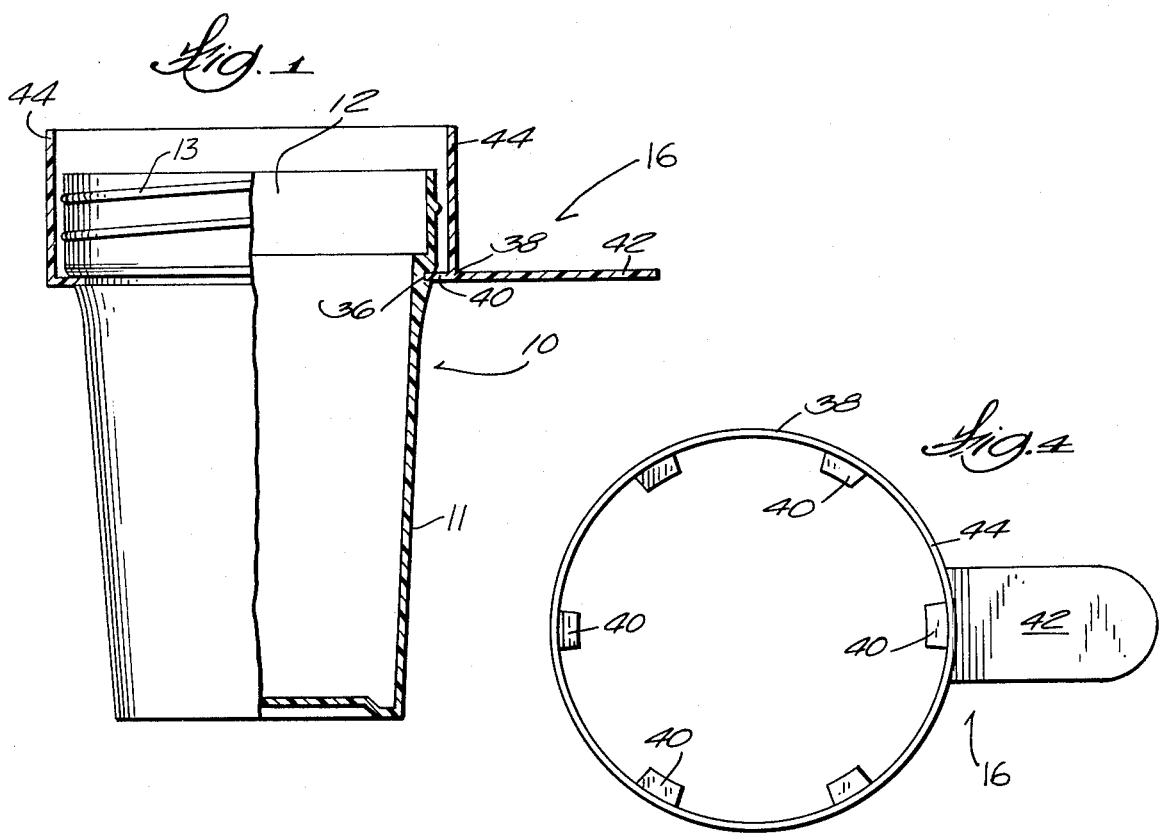
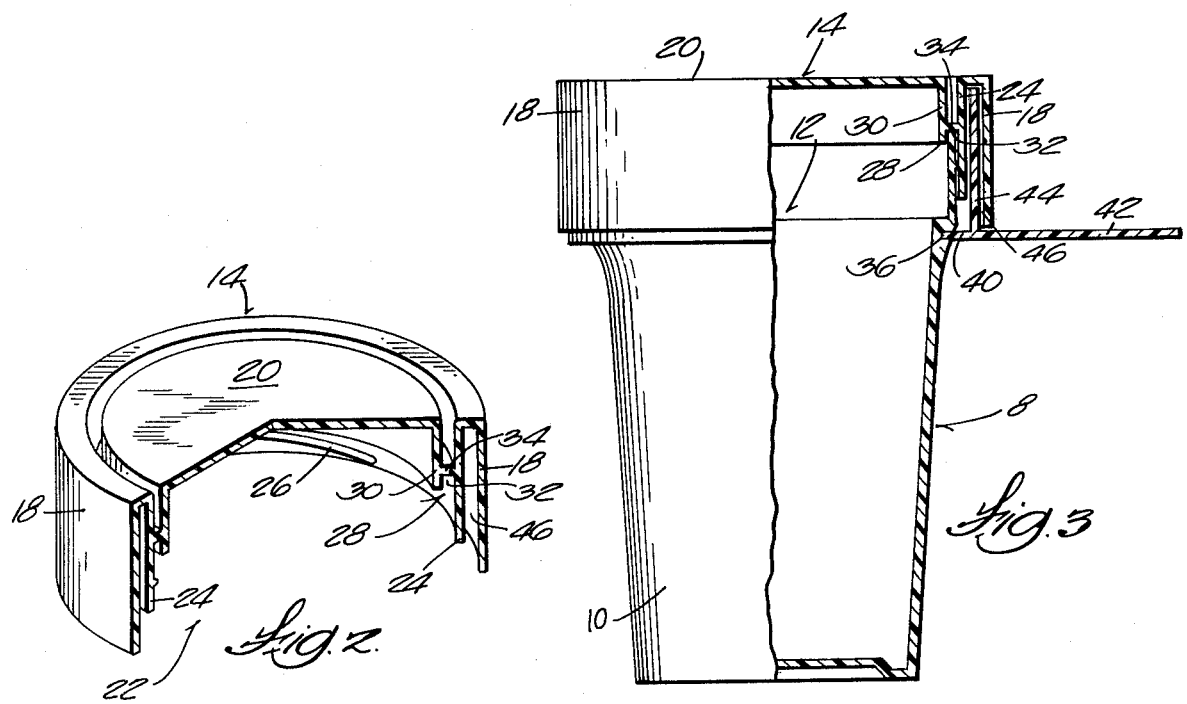

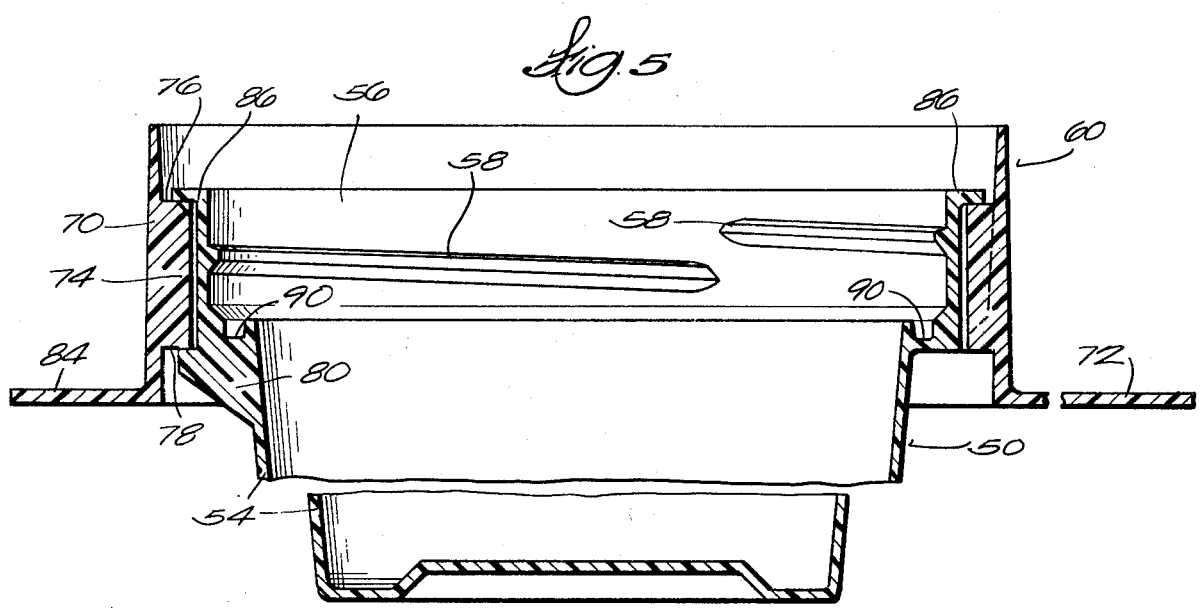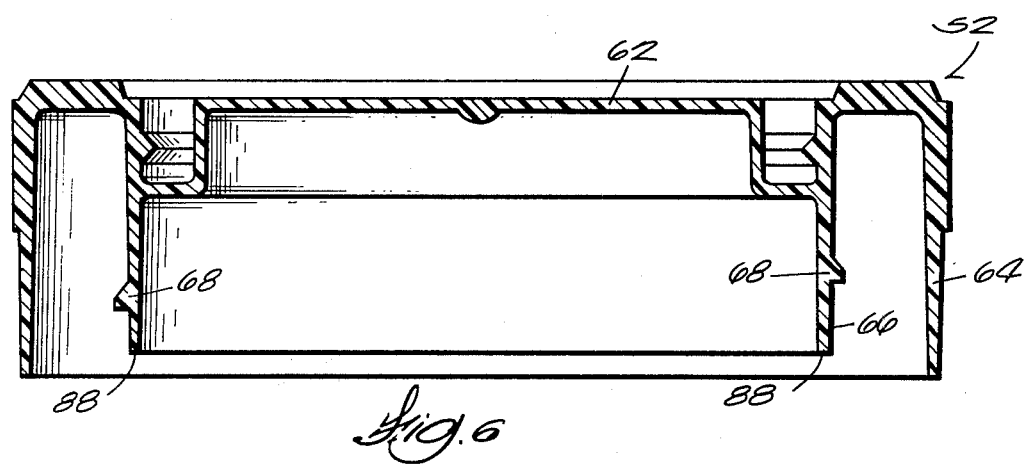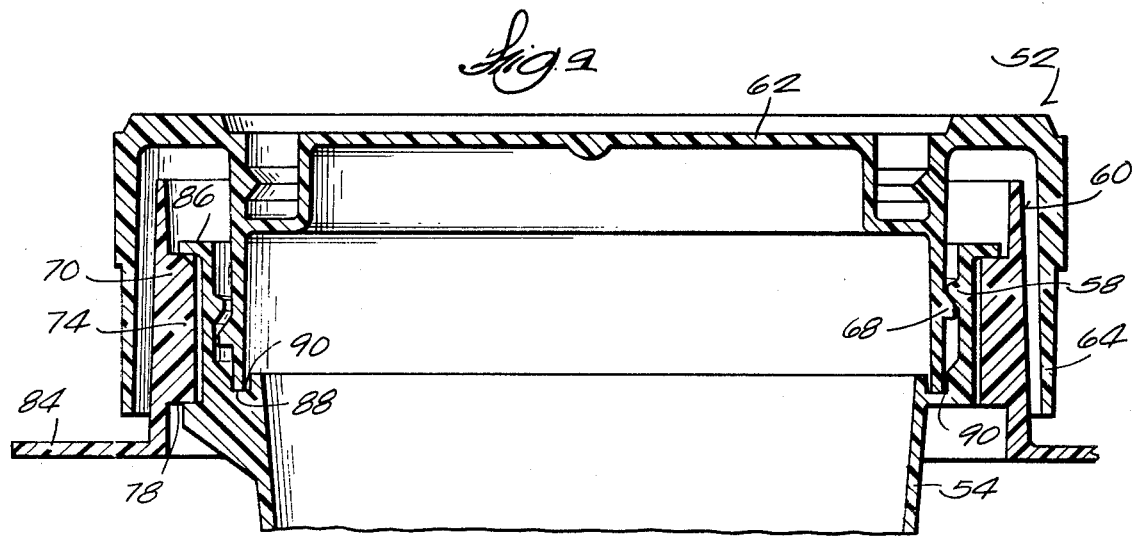

SPECIMEN COLLECTION ASSEMBLY

CROSS REFERENCE TO RELATED APPLICATION

This is a continuation-in-part application of application Ser. No. 910,643 filed May 30, 1978, now abandoned.

BACKGROUND OF THE INVENTION

This invention relates generally to medical specimen collection assemblies and, more particularly, to a medical specimen cup having a sealing cap member.

When using a medical specimen collection cup, such as for a urine sample, it is necessary to protect the specimen from contamination. The open end portion of the cup and the interior surfaces of the cap for such a cup are particularly vulnerable to hand and body contact or the like before, during, and after the collection of the specimen, which contact can ultimately contaminate the specimen. Conventional specimen cups do not shield these vulnerable areas from such contaminating contact in a simple manner, requiring no special handling.

SUMMARY OF THE INVENTION

It is one of the objects of this invention to shield the open end portion of a medical specimen collection cup from hand and body contact or the like to reduce the chances of contaminating the specimen.

It is another object of this invention to provide a cap for sealing a medical specimen collection cup, which cap also protects the interior surfaces of the cap, and thus the specimen itself, from contamination.

To achieve these and other objects, the invention provides a specimen collection assembly comprising a cup member having a body portion and an open end closure portion. The device further includes a cap member having a closure portion adapted for engagement with the cup closure portion to effectuate a seal between the cup member and the cap member. The cap member has a depending outer peripheral wall surrounding the cap closure portion and extending past and covering the outermost extremities of the cap closure portion. By virtue of this construction, the interior surfaces of the cap member are shielded from hand and body contact as the cap member is being engaged upon the cup member.

The cup member includes an outer protective wall extending past and covering the outermost extremities of the open end closure portion of the cup. The outer protective wall shields the open end closure portion from contaminating contact.

The outer protective wall on the cap member is in the form of a depending outer peripheral wall surrounding the cap closure portion and in which the outer protective wall on the cup member is in the form of an upstanding outer peripheral wall surrounding the cup closure portion. The upstanding outer peripheral protective wall on the cup member is a separate part adapted for snap engagement with the body of the cup member. The depending outer peripheral wall on the cap member surrounds the upstanding outer peripheral wall on the cup member when the cap and cup members are assembled in sealing engagement.

The cup member has a threaded open end closure portion and the closure portion of the cap member is similarly threaded to effectuate a threadable engagement between the cup member and the cap member.

DESCRIPTION OF THE DRAWINGS

FIG. 1 is a front elevation view, partly in section, of a cup member of a first embodiment of a medical specimen collection assembly;

FIG. 2 is a fragmentary perspective view of a cap member for the medical specimen collection assembly which cap member is adapted to seal the cup shown in FIG. 1;

FIG. 3 is a front elevation view, partly in section, of the entire medical specimen collection assembly with the cap member of FIG. 2 threadably received by the cup member of FIG. 1;

FIG. 4 is a top view of the protective lip assembly shown in FIG. 1;

FIG. 5 is an elevation view, partly in section, of the cup member of a second embodiment of a medical specimen collection assembly (with the combination protective wall and handle member mounted thereon);

FIG. 6 is a sectional view of a cap member for the collection device which cap member is adapted to seal the cup shown in FIG. 5;

FIG. 9 is an elevation view, partially in section, of the assembled medical specimen collection device with the cap member of FIG. 6 threadably received on the cup member of FIG. 5.

DESCRIPTION OF THE PREFERRED EMBODIMENTS

Figure 7:
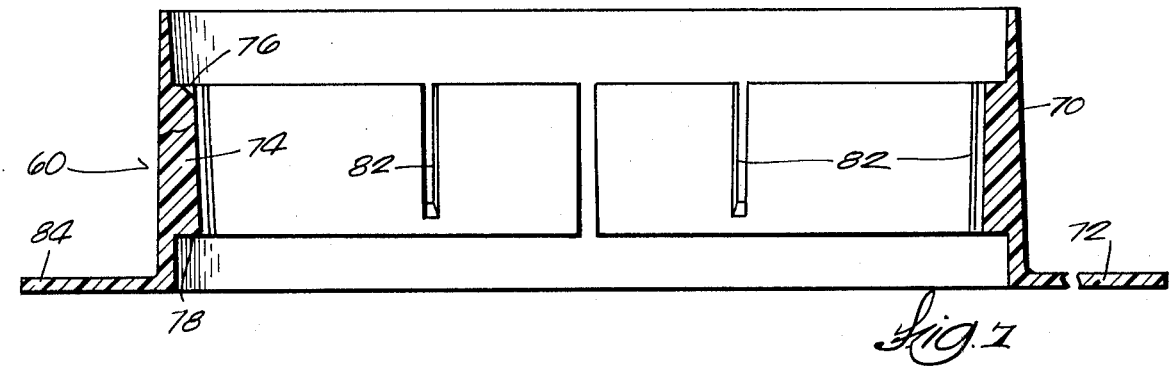
FIG. 7 is a sectional view of the combination protective wall and handle member shown in FIG. 5.
Figure 8:
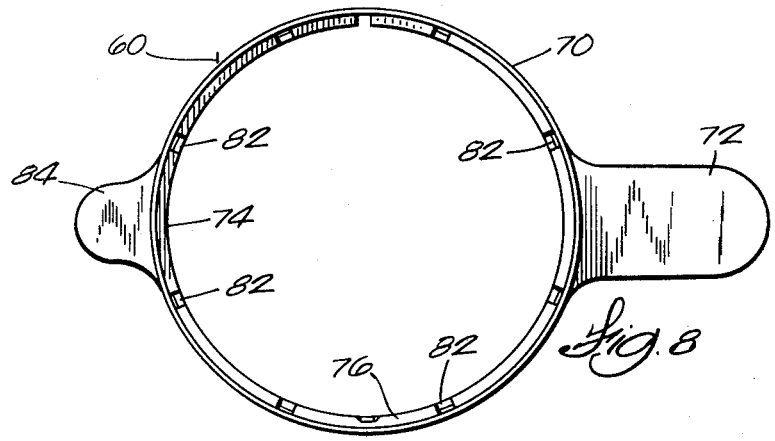
FIG. 8 is a top plan view of the combination protective wall and handle member shown in FIG. 7.

A medical specimen collection assembly 8 is shown in FIG. 3. The invention perhaps finds its widest application in connection with a urine specimen collection cup, and the invention will hereafter be discussed in that environment. However, it should be appreciated that the specimen collection assembly 8 is applicable for use in other environments.

When used to collect urine samples the assembly includes a cap 14 and a cup 10 having a body portion 11 and an end closure portion 12. End closure portion 12 is provided with threads 13. Referring to FIG. 2, the cap 14 includes an outer peripheral wall 18, a top portion 20 and an oppositely spaced open end 22 which is adapted to accommodate the end portion 12 of the cup 10. Preferably, the cap 14 is made of polyethylene, while the cup 10 is made of polypropylene material.

Cap 14 has an integral closure portion 24 which extends from the top portion 20 towards the open end 22. Closure portion 24 is concentric with and entirely encircled by the outer peripheral wall 18 and includes threads 26 thereon for engagement with the externally threaded end portion 12 of the cup 10 (see FIG. 3).

As best shown in FIG. 2, the vertical length of the closure portion 24, as measured from the top portion 20, is less than the comparable vertical length of the outer peripheral wall 18. Thus, when the cap 14 is placed upon a flat surface, only the edges of the outer peripheral wall 18 contact the surface. The chance of contaminating the interior surfaces of the cap 14, and in particular the threaded closure portion 24, is significantly reduced. Furthermore, because outer perimeter wall 18 completely encircles the closure portion 24, hand contact with the interior surfaces of the cap 14, both before and during the collection of the specimen, is prevented, which further enhances the sanitary features of the screw cap 14.

The cap 14 further includes sealing means 28 for preventing leakage of the specimen from the cup 10 when the cap 14 is threadably received thereon. In the illustrated embodiment, the sealing means 28 includes an inner partition portion 30 extending from the top portion 20 toward the open end 22, which partition portion 30 is concentric with and completely encircled by the closure portion 24. The portions 24 and 30 are spaced apart and a channel 32 is formed therebetween. A ledge 34 spans a portion of the channel 32 thereby joining the portions 24 and 30. As can be seen in FIG. 3, when the cap 14 is threadably received by the cup 10, the threaded end portion 12 is received by the channel 32 and abuts against the underside of the ledge 34, thereby forming an impervious interface to prevent leakage of specimen from the cup 10.

Referring next to FIG. 1, the cup 10 includes a generally vertically extending protective lip 44 which is concentric with and completely encircles the externally threaded end portion 12. The protective lip 44 is an integral part of a handle assembly 16. The handle assembly 16 is preferably made of polystyrene material and includes a circular main body 38 having a handle appendage 42 and a plurality of inwardly facing tabs 40. The cup 10 includes a groove 36 about its periphery and the tabs 40 are adapted to be snap-fitted within the peripheral groove 36, thereby removably attaching the circular main body 38, and thus the protective lip 44, upon the cup 10. Just as the outer peripheral wall 18 of the cap 14 reduces the chance of contaminating the interior surfaces of the cap 14, the protective lip 44 shields the threaded end portion 12 of the cup 10 from hand contact and the like when the specimen is being taken, thereby enhancing the protection of the specimen from contamination. Furthermore, the tabs 40, in lieu of a continuous ledge, prevent trapping the specimen in the space between the protective lip 44 and the threaded end portion 12, thereby permitting drainage should accidental spill over occur.

As shown in FIG. 3, the cap 14 is adapted to accommodate the vertically projecting protective lip 44. Because the outer peripheral wall 18 and the first inner partition member 24 are spaced apart, a channel 46 is defined therebetween. The protective lip 44 is received by the channel 46 as the cap 14 is being threadably received by the cup 10.

It will be appreciated that while in the preferred embodiment described above, a screw-type closure between the cup and the cap is used, other types of closures such as a snap-type closure can be used without departing from the invention herein. Also, it will be appreciated, while in the preferred embodiment the protective lip 44 and handle assembly 16 is a separate part, such assembly can be made integrally with the body of the cup 10.

FIGS. 5-11 show a second embodiment of the present invention. Such second embodiment includes a cup member 50 (FIG. 5) and a cap member 52 (FIG. 6). Cup member 50 includes a body portion 54 and an end closure portion 56. End closure portion 56 is provided with threads 58 on the internal surface thereof and is also provided with a circular lip 86 around the upper edge thereof. As shown in FIG. 5, a combination protective wall and handle member 60 is mounted on the end closure portion 56.

As best shown in FIG. 6, cap member 52 includes a top portion 62 having a depending outer wall 64 and a concentric depending inner wall 66. Wall 66 has threads 68 on the external surface thereof.

Preferably, cap member 52 is made of polyethylene, cup member 50 is made of polypropylene and combination protective wall and handle member 60 is made of polystyrene.

As best shown in FIG. 6, the vertical length of outer peripheral wall 64 of the cap member is greater than that of the inner wall 66; thus, when the cap 52 is placed upon a flat surface, only the edges of the outer wall 64 will contact the supporting surface. The chance of contaminating the interior surface of the cap member is thereby significantly reduced. Furthermore, because outer wall 64 completely encircles the inner wall 66, hand contact with the interior surfaces of the cap 52 both before and during the collection of the specimen, is prevented. This further enhances the sanitary features of the cap member 52.

Combination protective wall and handle member 60 is comprised of a protective wall portion 70 and a handle portion 72. As best shown in FIG. 5, protective wall portion 70 has an inwardly extending circular belt portion 74 formed thereon which provides upwardly and downwardly facing shoulders 76 and 78.

Snap-on engagement of member 60 on cup member 50 is accomplished by means of the cooperative interrelationship of shoulders 78 on member 60 with a plurality of annularly spaced, radially extending retaining ribs 80 formed integrally with the exterior surface of cup 50. The circular belt portion 74 is provided with a plurality of annularly spaced grooves 82 (FIG. 8) positioned for alignment with ribs 80.

To assemble member 60 on cup 50, the cup is inserted through the top of member 60, grooves 82 are aligned with ribs 80 and then the parts are snapped into place as shown in FIG. 5, with the top surface of the ribs in engagement with the shoulder 78 on member 60. Removal of member 60 from the cup member 50 can be accomplished by the reverse procedure. A small tab 84 on member 60 is provided to facilitate the removal of member 60 from the cup 50.

Just as the outer peripheral wall 64 of cap 52 reduces the chance of contaminating the interior surfaces of the cap 14, the protective wall 70 on member 60 shields the threaded end portion 56 of cup 50. The circular lip 86 at the top of threaded end portion 56 cooperates with the shoulder 76 on member 60 to seal the parts together and thus prevent any accidental leakage of urine between member 60 and end portion 56.

A seal between cap 52 and cup 50 is provided by the cooperation of end surface 88 on wall 66 of cap 52 with a groove 90 in end portion 56 of cup 50. Thus, as the threads 58 and 68 on cup 50 and cap 52, respectively, are engaged by screwing the cap onto the cup, surface 88 will seat in groove 90 to thereby seal the cap to the cup.

Figure 10:
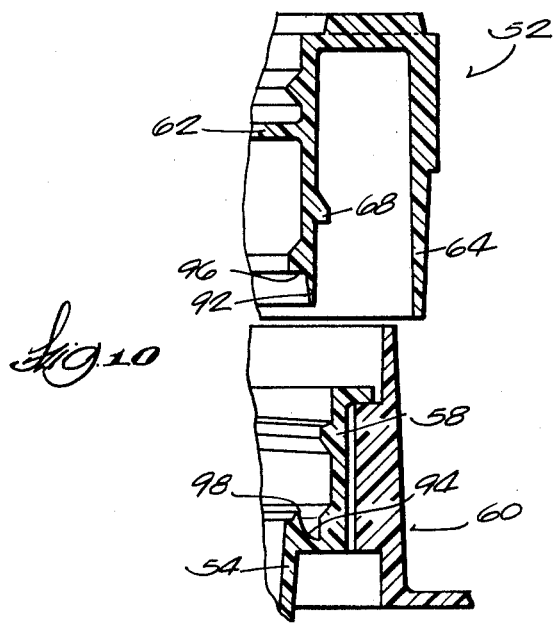
FIGS. 10 and 11 are fragmentary sectional views showing an alternate construction for sealing the cap member with the cup member.
Figure 11:
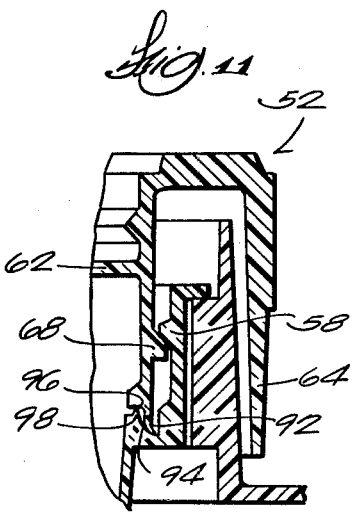

An alternative seal arrangement is shown in FIGS. 10 and 11. A shown, a tapered edge portion 92 is provided on the end of wall 66 which is dimensioned to cooperate with a groove 94 in the cup. When the cap is screwed onto the cup as shown in FIG. 11, the end of the tapered edge portion 92 will move into sealing engagement with groove 94 as end portion 92 becomes slightly deformed.

Also, the small shoulder 96 at the base of tapered edge portion 92 will seat against a cooperating shoulder stop surface 98 adjacent groove 94. The secondary seal is thus provided by the engagement of shoulder 96 on surface 98. Surface 98 also serves as a stop to control and limit the amount of deformation of the tapered edge portion 92 when the cap is screwed onto the cup as shown in FIG. 11.

In use, a specimen is taken with combination protective wall and handle member 60 installed on cup 50 as shown in FIG. 5. The cup is conveniently held by the user during the taking of the specimen by the use of handle portion 72 on member 60. As indicated previously, the abutting relationship of lip 86 against shoulder 76 prevents any accidental leakage of urine between member 60 and the closure portion 56 of cup 50. After the specimen is taken, cap 52 is screwed onto cup 50 causing surface 88 on wall 66 to seat in groove 90 to thereby establish a seal between the cup and the cap.

As previously explained, during the taking of the specimen and the installation of the cap on the cup, the interior surfaces of the cap and the cup are protected against touch contamination by protective wall 64 on the cap and the protective wall 70 on member 60.

After the cap is installed on the cup, the combination protective wall and handle member 60 has no further function and can be removed by simply pressing downwardly on handle portion 72 and tab 84 causing member 60 to be forced out of snap engagement with retaining ribs 80. Removal of member 60 facilitates further handling and storage of the cap and cup assembly. The ability to remove member 60 after sealing assembly of cap and cup results in a cleaner and safer handling procedure. Also with member 60 removed the specimen can be poured out of the cup over the previously protected and thus uncontaminated lip 86.

We claim:

1. A specimen collection assembly comprising:
   a cup member having a body portion and an upper end cup closure portion, said cup member further having an outer protective wall spaced from said cup closure portion and extending vertically beyond the upper edge of said closure portion;
   a cap member having a top portion and a cap closure portion, said cap member further having an outer protective wall spaced from said cap closure portion and extending vertically beyond the bottom edge of said cap closure portion;
   connection means on said cup and cap closure portions to connect said cap member to said cup member; and sealing means for sealing said cap member on said cup member when said cap member and said cup member are connected to each other by said connection means.

2. A specimen collection assembly according to claim 1, in which said outer protective wall on said cap member is in the form of a depending outer peripheral wall surrounding said cap closure portion and in which said outer protective wall on said cup member is in the form of an upstanding outer peripheral wall surrounding said cup closure portion.

3. A specimen collection assembly according to claim 2, in which said depending outer peripheral wall on said cap member surrounds said upstanding outer peripheral wall on said cup member when said cap and cup members are assembled in sealing engagement.

4. A specimen collection assembly according to claim 2, in which said upstanding outer peripheral wall on said cup member is a separate member adapted for snap engagement with the body of said cup member.

5. A specimen collection assembly according to claim 4 in which said separate member has a handle portion formed thereon.

6. A specimen collection assembly according to claim 4 in which said upstanding outer peripheral wall on said separate member is spaced from said depending outer peripheral wall on said cap member so that said separate member can be removed from said cup member with said cup and cap members connected together.

7. A specimen collection assembly according to claim 1 in which said connection means is comprised of mating threads formed on said cup and cap closure portions.

8. A specimen collection assembly according to claim 7 in which the thread on said cup closure portion is formed on the external surface thereof and the thread on said cap closure portion is formed on the internal surface thereof.

9. A specimen collection assembly according to claim 7 in which the thread on said cup closure portion is formed on the internal surface thereof and the thread on said cap closure portion is formed on the external surface thereof.

10. A specimen collection assembly according to claim 1 in which said sealing means is comprised of the upwardly facing top edge of said cup closure portion and a downwardly facing ledge formed on said cap closure portion, said upwardly facing top edge and said ledge cooperating to form a seal between the cup and cap when said cap is connected to said cup by said connection means.

11. A specimen collection assembly according to claim 1 in which said sealing means is comprised of an upwardly facing groove formed in said cup member and the downwardly facing bottom edge on said cap closure portion, said upwardly facing groove and said downwardly facing bottom edge cooperating with each other to form a seal between the cap and the cup when said cap and cup are connected together by said connection means.

12. A specimen collection assembly according to claim 11 in which said sealing means is further characterized by a tapered portion at the bottom end portion of said cap closure portion which tapered portion becomes slightly deformed as said cap and cup are connected together by said connection means.

13. A specimen collection assembly according to claim 4 in which said upper end cup closure portion has a circular lip formed at the top edge thereof and in which said separate member has a shoulder formed thereon which abuts said circular lip, said abutting relationship serving to prevent leakage of liquid between said separate member and said cup closure portion.

* * * * *